United States Patent [19]

Kaelble

[11] 4,204,325
[45] May 27, 1980

[54] ORTHODONTIC BRACKET BONDING SYSTEM

[75] Inventor: David H. Kaelble, Thousand Oaks, Calif.

[73] Assignee: Arroyo Research and Consulting Company, La Canada, Calif.

[21] Appl. No.: 905,198

[22] Filed: May 12, 1978

[51] Int. Cl.² ............................................... A61C 7/00
[52] U.S. Cl. ...................................................... 433/9
[58] Field of Search ............... 156/249, 344; 32/14 C, 32/14 D, 14 B, 14 A, 15; 428/40

[56] References Cited

U.S. PATENT DOCUMENTS

| | | | |
|---|---|---|---|
| 3,191,303 | 6/1965 | Baum | 32/15 |
| 3,250,002 | 5/1966 | Collito | 32/15 |
| 3,490,145 | 1/1970 | Charrier et al. | 32/14 A |
| 3,504,438 | 4/1970 | Wittman et al. | 32/14 A |
| 3,532,652 | 10/1970 | Zang et al. | 428/40 |
| 3,639,500 | 2/1972 | Muny et al. | 428/40 |
| 3,745,653 | 7/1973 | Cohl | 32/14 A |
| 3,797,115 | 3/1974 | Silverman et al. | 32/14 A |

OTHER PUBLICATIONS

"Polysulfone Hollow Fibers," Cabasso et al., 20, J. App. Poly. Sci., 1976, pp. 2377–2387, 2393–2394.
"Spin Casting of Polymer Films," Kaelble, 9, J. App. Poly. Sci., 1965, pp. 1209–1212.

Primary Examiner—Louis G. Mancene
Assistant Examiner—Michael J. Foycik, Jr.

[57] ABSTRACT

Orthodontic brackets are adhered to the surface of tooth enamel by activating the surface of an adhesive patch and applying the activated surface to the enamel. The adhesive patch may be preformulated and prefabricated into a solid film sandwiched between easy release protective liners and the film can be applied to the bracket by surface activation as discussed above. The invention also includes removal of the bracket by a deactivation of the surface of the adhesive patch.

11 Claims, 11 Drawing Figures

Fig. 5a. PREPARE ENAMEL SURFACE
Fig. 5b. STRIP FRONT COVER SHEET
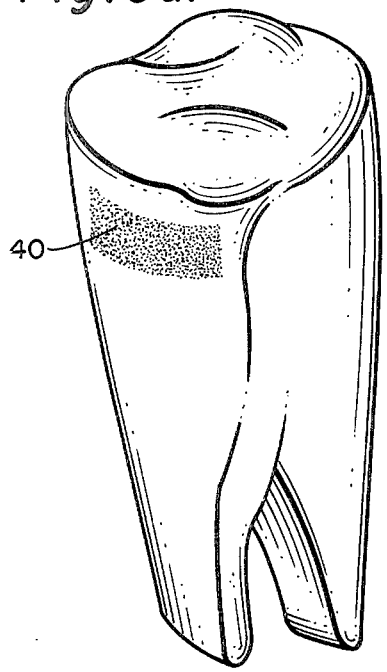
Fig. 5c. ACTIVATE SURFACE
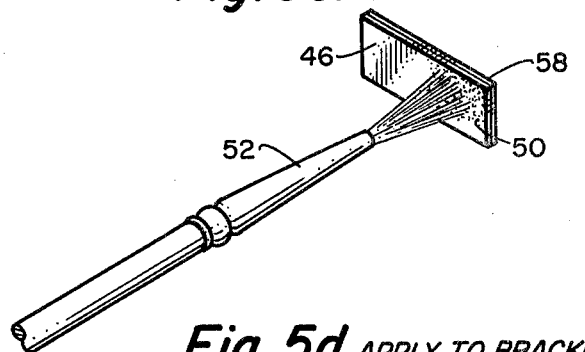
Fig. 5d. APPLY TO BRACKET
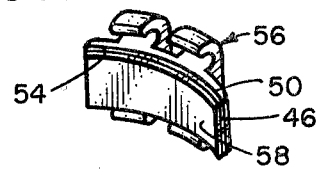
Fig. 5g. BOND TO ENAMEL
Fig. 5e. STRIP REAR COVER SHEET
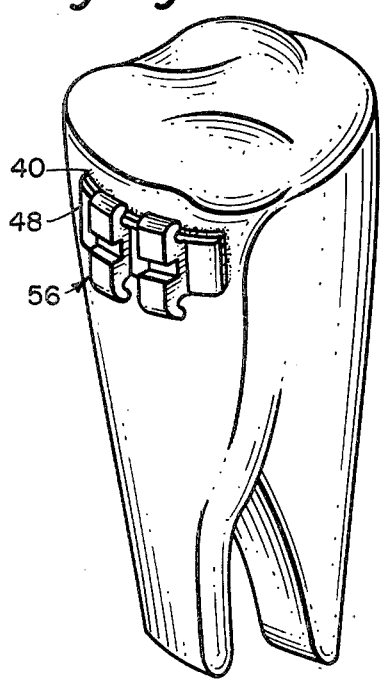
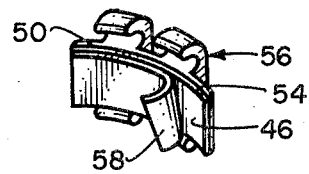
Fig. 5f. ACTIVATE SURFACE
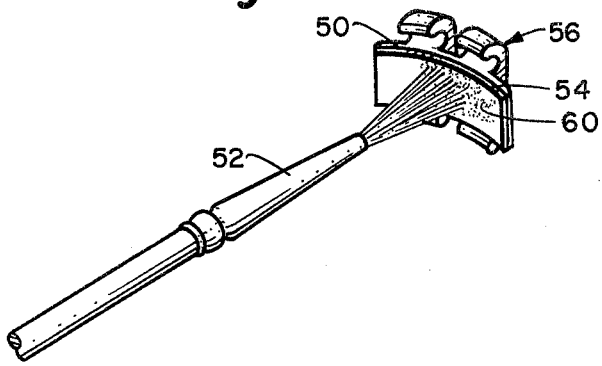

ORTHODONTIC BRACKET BONDING SYSTEM

BACKGROUND OF THE INVENTION

1. Field of the Invention

The present invention relates to the application of orthodontic brackets to the surface of tooth enamel and, more particularly, to adhesive systems and the formulation, activation and deactivation of such systems.

2. Description of the Prior Art

Adhesive systems for bonding orthodontic brackets to teeth appear to have been produced as an afterthought and as a derivative technology of dental cements and sealants.

Many of the desired properties of a bracket adhesive appear unavailable in present commercial bracket adhesives which require preparation of enamel by etching, thorough and critical mixing of two component liquid adhesives, constantly changing viscosity and limited pot life and subsequent slow setting by chemical reaction. Furthermore, the present adhesive systems are generally designed for permanent bonding and therefore do not provide a mechanism for removal which avoids damage to the teeth.

There is a present need for an adhesive system specifically developed to bond othodontic brackets to teeth. This adhesive should be simple to apply, perform a holding function with high reliability for variable periods, then be easily removed by mechanical or chemical means without damage to the enamel surface.

SUMMARY OF THE INVENTION

The present invention provides dry adhesive systems for application of dental brackets to teeth. Critical mixing of liquid ingredients and short pot lives are avoided. The adhesives are activated by application of reagent to the adhesive and/or to the surface of the tooth enamel. The adhesive may be prepackaged in rolls and cut to size or in precut patches with protective release films on each surface or a patch of adhesive may be preapplied to the rear surface of the bracket.

The adhesives can readily be removed without damage to the enamel by an application of a deactivation reagent to the bonded surfaces. The adhesive system of the invention is simple to apply, provides a high reliability bond, yet is readily removed without damage to the enamel surface.

These and many other features and attendant advantages of the invention will become apparent as the invention becomes better understood by reference to the following detailed description when considered in conjunction with the accompanying drawings.

BRIEF DESCRIPTION OF THE DRAWINGS

FIGS. 5(a) through 5(g) are a combination chart and schematic illustration of the process of the invention.

DESCRIPTION OF THE PREFERRED EMBODIMENTS

Figure 1:
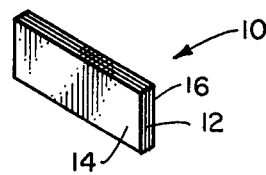
FIG. 1 is an end view in elevation of the adhesive film patch of the invention.
Figure 2:
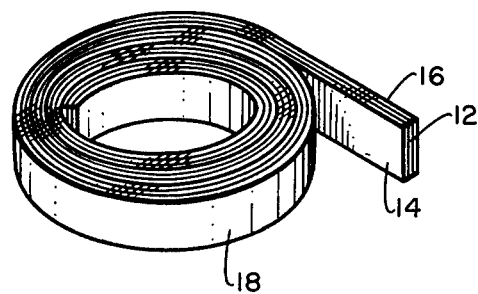
FIG. 2 is an end elevational view of a continuous roll form of the adhesive.
Figure 3:
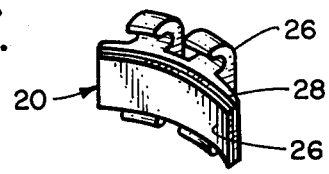
FIG. 3 is an end elevational view of a patch adhered to an orthodontic bracket.
Figure 4:
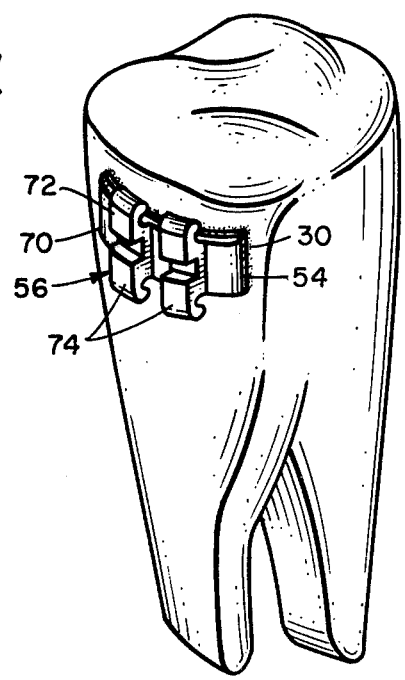
FIG. 4 is an edge view in section of a bracket adhered to tooth enamel with the adhesive patch of the invention.

Referring now to FIG. 1, the orthodontic bracket adhesive is a patch 10 sized for the particular application. The patch is formed of a layer of solid resilient adhesive 12, having each surface covered with a manually strippable cover film 14, 16 of a protective material such as a vinyl, Teflon or polyeyhylene film. The patches 10 may be marketed in precut form such as narrow or medium lateral/anterior medium or wide cuspid or bicuspid, molar or central brackets to cover the complete dental arch or as shown in FIG. 2 the adhesive may be supplied in sheet or roll form 18 and cut to desired configuration by the Orthodontist or his technician or assistant. Another very convenient form of use would be to preapply the adhesive patch 20 to the rear surface 24 of a bracket 26 as shown in FIG. 3. Only the rear cover film 26 need be stripped and the surface 28 of the adhesive and/or mating surface 30 of the tooth enamel activated to complete an installation as shown in FIG. 4.

A technique procedure is illustrated in FIG. 5. The surface 40 of the enamel is prepared according to usual orthodontic practice by polishing, rinsing, etching with 50% phosphoric acid, rinsing, and air drying. Sealing the enamel need not be practiced. The front cover film 42 of the adhesive patch 44 is pulled off and discarded. The front surface 46 of the adhesive film 48 is activated by applying a liquid layer 50 of activator from a brush 52 or other coating method such as pad, roller or dipping.

The activated surface 46 is then applied to the rear surface 54 of a bracket 56. After the bond has set, the rear release film 58 is stripped from the adhesive film 48 and the surface 60 of the adhesive film is activated by means of brush 52. The activated surface 60 is then applied to the etched surface 40 of the tooth enamel.

It is apparent that the bracket adhering technique of this invention eliminates mixing, proportioning, solvent purge, critical pot life, critical open time for reagents and clean-up problems. The method of this invention utilizes ambient temperature application and cure providing minimum bond strength for handling in minutes and tough complete bonds in a short period of 1 to 3 hours. The brackets for each patient can be organized and prepared for enamel bonding before the patient's appointment. Excessive adhesive overhanging or exuding from under the bracket are also avoided. The technique results in neat, clean, attractive hygienic appliances.

The adhesive film patch is utilizable with any dental appliance that is to be adhesively secured to enamel, particularly orthodontic brackets. Referring again to FIG. 4 the bracket 56 is formed of a base plate 70, usually curved, having a rear concave surface 54 for attaching to tooth enamel. The front surface 72 of the bracket carries fasteners 74 of various types such as hooks or fasteners for engaging wires, tubes, adhesive bonds or cords.

The adhesive film incorporated in the patch is a solid, resilient, continuous film of organic resin material capable of surface activation by liquid to produce a temporary state of high tack capable of aggressive bonding to the orthodontic bracket and tooth enamel. The adhesive film returns to the normal holding state in a few seconds to a few minutes. The activation of one surface does not affect the other surface. Therefore the bracket-patch assembly with rear release film can be stored for later use.

The holding state is retained until the film is reactivated. Removal of the bracket could occur at any time without damage to the tooth surface by reactivating the adhesive at the edge of the bond and applying light lifting pressure to the bracket. This mechanism could be applied to experimentally relocate the bracket during initial installation or subsequent to long term service.

It is understood that the adhesive system would present required direct bonding ability, bond strength and creep resistance, resistance to variables of oral environment, and be generally inert and nontoxic.

The adhesive film must be capable of temporary activation by liquid reagent and be capable of deactivation with liquid reagent to permit removal from the enamel. The film can be selected from resilient linear polymers such as acrylic copolymers, ionomer carboxylate salt resins, linear phenoxy or polyethersulfones (PES). These polymers can be surface activated with special reagents which are a combination of resin soluble solvent, resin swelling solvent and resin insoluble solvent. For example, polyethersulfone can be activated and deactivated with a reagent comprising in weight percent 40%–60% methylene chloride, 35%–50% chloroform and 1%–8% methanol. Other suitable systems can be selected from the Polysulfone solubility map disclosed by I. Cabasso et al, "Polysulfone Hollow Fibers Spinning Properties", J. Appl. Poly Sci., 20 2377 (1976), the disclosure of which is expressly incorporated herein by reference.

The adhesive film of the invention may also be formulated from reactive adhesives in which prepolymers or polymers are surface activated by curing agent, catalyst or cross-linking agent. Some of these systems are based on methacrylate monomers and cure by free radical reactions rather than addition polymerization. Such systems have recently been introduced by several companies and offer the features of handling and cure properties desired in this invention.

Surface energy analysis was conducted on smooth film surfaces of test polymers using published test methods (J. Poly Sci., A-2 9, (1971) and J. Poly Sci., Poly. Phys. Ed., 11, 785 (1973). A special test was developed to test adhesion to ivory (elephant dentive) by the simple lap shear test.) Ivory plates were bonded to $\frac{1}{8}"\times 1"\times 4"$ aluminum alloy plates with Devcon 5 min. Epoxy adhesive and sanded with 600 grit Silicon carbide surface paper. This test permitted simple and reproducible tests of adhesive activation and bond strength with an easily interpreted result. A uniform thin film of PES 100P resin having a Tg of 250° C. was cast from solution using a special centrifugal casting method described by Kaelble (J. Appl. Poly. Sci., 9, 1209 (1965) for use in solvent activation and bonding studies.

A summary of surface energy analysis for PES 100P is presented in Table 1.

Table 1

| Adhesive Film Test Liquid | Surface Energy Analysis | |
|---|---|---|
| | $\gamma LV$ dyn/cm | PES 100P Advancing Contact Angle (Degrees) |
| Water | 72.8 | 57 |
| Glycerine | 64.0 | 57 |
| Formamide | 58.3 | 48 |
| Eth. Glycol | 48.3 | 46 |
| 1-Br-Naphthalene | 44.6 | 15 |

Table 1-continued

| Adhesive Film Test Liquid | Surface Energy Analysis | |
|---|---|---|
| | $\gamma LV$ dyn/cm | PES 100P Advancing Contact Angle (Degrees) |
| E-200 | 43.5 | 23 |
| TCP | 40.9 | 11 |
| E-15-20 | 36.6 | 19 |
| E-1200 | 31.3 | 19 |
| Hexadecane | 27.6 | 16 |
| Solid Surface Tensions | | |
| $\gamma^d \pm \delta^d$ (dyn/cm) | | 28.0 ± 2.4 |
| $\gamma^p \pm \delta^p$ | | 14.9 ± 2.4 |
| $\gamma + \delta$ | | 42.9 ± 0.9 |

The lower portion of Table 1 summarizes the calculated values of dispersion —d and polar —p contibutions to solid surface tension $\gamma=\gamma^d+\gamma^p$ as well as the calculated values for the standard deviations from the means $\delta^d,\delta^p$, and $\delta$. These results show that PES resin has high surface tension and polar response $\gamma^p$.

A summary of bond strength data using the ivory adherend lap shear test is presented in Table 2.

Table 2

| Bond Strength to Ivory in Lap Shear at 22° C. | | | |
|---|---|---|---|
| Adhesive: PES | | | |
| Test | $\epsilon_y$(cm) | $\sigma_y$(psi) | Drying Condition |
| 1 | ~0.050 | 16 | two hour dry |
| 2 | ~0.15 | 225 | weekend dry |
| 3 | ~0.10 | 72 | weekend dry |
| 4 | ~0.10 | 143 | two hour 60° C. |
| 5 | ~0.14 | $\frac{235}{138}=\sigma_y(ave)$ | two hour 60° C. |
| Adhesive: Weldmaster* | | | |
| Test | $\epsilon_y$(cm) | $\sigma_y$(psi) | Failure |
| 1 | 0.055 | 616 | interfacial |
| 2 | 0.047 | 358 | interfacial |
| 3 | ~0.070 | >650 | not broken |
| 4 | 0.070 | 466 | interfacial |
| 5 | 0.035 | 201 | uncured |

*Reactive Adhesive - National Starch and Chemical Corp.
$\epsilon_y$ = the shear displacement of the bond at yielding or failure
$\sigma_y$ = the shear stress of the bond at yielding or failure Bonding Method Ivory sanded with 600 grit silicon carbide paper, water rinsed and air dried. a 0.007 to 0.015 inch thick film of bonding material is cut to size 0.5×1.0 inch and activated by cotton swab of solvent on one side and adhered to ivory. Second side is thin activated by solvent swab and two ivory surfaces bonded by light hand pressure.

For Weldmaster bonding involved following manufacturers recommended procedure to apply adhesive to one ivory surface, activator to the second and gently press together to initiate curing reaction.

The average strength of PES 100P is raised by extending the drying time or raising the drying temperature. The activator utilized comprised 53% methylene chloride (solvent) 43% chloroform (swelling) and 4% methanol (non-solvent). The paper by Cabasso et al, referenced above, displays the solubility range for polysulfone polymers in terms of the three component solubility parameters:

$$\delta^2=\delta_d^2+\delta_p^2+\delta_h^2$$

where the subscripts respectively denote dispersion —d, polar —p, and hydrogen —h bonding contribution to the cohesive energy density $\delta^2$. The solvent activation system lies well within the dished curve defining the area of solubility in the reference indicating the content of non-solvent such as methanol should be increased and/or a less soluble solvent should be utilized in the activator system to prevent overactivation and swelling. The solvent system described could be utilized for deactivation and removal of the PES 100P adhesive patch from enamel.

The shear test results of the Weldmaster adhesive are notable in giving a consistent high level of strength. Experience with this adhesive demonstrated full cure in 24 hours and substantial strength in three hours.

It is to be realized that only preferred embodiments of the invention have been described and that numerous substitutions, modifications and alterations are permissible without departing from the spirit and scope of the invention as defined in the following claims.

What is claimed is:

1. A method of adhering orthodontic brackets to the surface of tooth enamel comprising the steps of:
   removing a protective cover sheet from the surface of a patch of dry, solid, resilient, continuous film of organic resin adhesive secured to the rear surface of the bracket;
   activating the exposed surface of the dry adhesive film by applying a liquid activating reagent to the surface to produce a temporary state of high tack capable of aggressive bonding to the tooth enamel without affecting the rear surface of the film;
   applying the activated surface of the adhesive film to the surface of the tooth enamel and forming an interfacial bond between the surfaces.

2. A method according to claim 1 in which the film of adhesive patch has a thickness from 1 to 10 mils.

3. A method according to claim 2 in which the liquid reagent penetrates into the adhesive film no more than 50% of the thickness of the film.

4. A method according to claim 2 in which the polymer is a linear polymer.

5. A method according to claim 4 in which the polymer is a polyethersulfone.

6. A method according to claim 5 in which the liquid reagent is a combination of a resin soluble solvent, resin swelling solvent and resin insoluble solvent.

7. A method according to claim 6 in which the reagent comprises in weight percent, 40% to 60% methylene chloride, 35% to 50% chloroform and 1% to 8% methanol.

8. A method according to claim 2 in which the protective cover sheet is a continuous manually peelable continuous sheet having a thickness from 1 to 5 mils and having a tensile strength greater than the bonding strength to the surface of the adhesive.

9. A method according to claim 8 in which the adhesive patch has cover sheets applied to the front and rear surfaces thereof and further including the step of peeling the rear cover sheet, activating the rear surface of the adhesive patch and applying the activated surface to the rear surface of the orthodontic bracket.

10. An method according to claim 6 in which the film comprises a 1 to 10 mil thick film of polyethersulfone.

11. A method according to claim 1 in which the activated surface returns to a first holding state in from a few seconds to a few minutes.

* * * * *